(12) United States Patent
Schwimmer et al.

(10) Patent No.: US 11,946,479 B2
(45) Date of Patent: Apr. 2, 2024

(54) WEARABLE COOLING DEVICE

(71) Applicants: Rachel Schwimmer, Los Angeles, CA (US); Ashley Elizabeth Berg, Houston, TX (US); Drew Eric Lilley, Chatham, NJ (US); Nicholas Paul Demes, New York, NY (US); Daniel Charles Bravo Harris, Philadelphia, PA (US); Samuel Gaardsmoe, Hellertown, PA (US)

(72) Inventors: Rachel Schwimmer, Los Angeles, CA (US); Ashley Elizabeth Berg, Houston, TX (US); Drew Eric Lilley, Chatham, NJ (US); Nicholas Paul Demes, New York, NY (US); Daniel Charles Bravo Harris, Philadelphia, PA (US); Samuel Gaardsmoe, Hellertown, PA (US)

(73) Assignees: Rachel Schwimmer, Venice, CA (US); Ashley Berg, Brooklyn, NY (US); Samuel Gaardsmoe, Philadelphia, PA (US)

( * ) Notice: Subject to any disclaimer, the term of this patent is extended or adjusted under 35 U.S.C. 154(b) by 768 days.

(21) Appl. No.: 16/257,328

(22) Filed: Jan. 25, 2019

(65) Prior Publication Data

US 2019/0234412 A1    Aug. 1, 2019

Related U.S. Application Data

(60) Provisional application No. 62/623,158, filed on Jan. 29, 2018.

(51) Int. Cl.
    *F04D 25/08*    (2006.01)
    *F04D 25/06*    (2006.01)
    (Continued)

(52) U.S. Cl.
    CPC ....... *F04D 25/084* (2013.01); *F04D 25/0673* (2013.01); *A41D 13/0025* (2013.01); *F04D 29/644* (2013.01); *F16M 13/04* (2013.01)

(58) Field of Classification Search
    CPC .............. A41D 13/005; A41D 13/0051; A41D 13/0053; A41D 13/0056; A41D 13/0058;
    (Continued)

(56) References Cited

U.S. PATENT DOCUMENTS

| 7,721,349 B1 | 5/2010 | Strauss |
| 7,785,359 B2 | 8/2010 | Latham |

(Continued)

OTHER PUBLICATIONS

U.S. Appl. No. 62/623,158, filed Jan. 29, 2018.

*Primary Examiner* — Bryan M Lettman
*Assistant Examiner* — Charles W Nichols
(74) *Attorney, Agent, or Firm* — McCarter & English, LLP

(57) ABSTRACT

A wearable cooling device that is designed to rapidly restore and/or maintain a user's thermal comfort is provided. The disclosed wearable cooling device is versatile and may be affixed to or in contact with (or close proximity to) a variety of locations on a user's body, e.g., wrist, neck and ankle, among others. The wearable cooling device utilizes a forced air device, e.g., a fan, that blows air onto a wetted piece of media, e.g., fabric, which is in direct contact with a high thermally conductive element, e.g., copper or aluminum. The high thermally conductive element may be in contact with a user's skin or with a user's outer clothing. The wetted media is situated between the forced air device and the high thermally conductive element. When the forced air device is activated, the exhaust air passes onto and around the wetted media, which in turn cools the high thermally conductive element. As a result, the high thermally conductive element cools down the user.

22 Claims, 3 Drawing Sheets

(51) Int. Cl.
*A41D 13/002* (2006.01)
*F04D 29/64* (2006.01)
*F16M 13/04* (2006.01)

(58) Field of Classification Search
CPC .......... A41D 13/0025; A41D 19/01541; A41D 20/005; F04D 25/0673; F04D 25/082; F04D 25/084; F04D 29/58; F04D 29/5826; F04D 29/584; F04D 29/588; F04D 29/5866; F04D 29/644; F16M 13/04; A47G 9/0215; A62B 17/005; A42B 1/008; A42B 3/285; A61F 7/00; A61F 7/02; A61F 2007/0068; A42C 5/04; F25D 7/00; F25D 2400/26
See application file for complete search history.

(56) References Cited

U.S. PATENT DOCUMENTS

| | | |
|---|---|---|
| 7,866,177 B2 | 1/2011 | Selm et al. |
| 9,029,736 B2 | 5/2015 | Lavin, Jr. |
| 2004/0083526 A1* | 5/2004 | Ichigaya ............ A41D 13/0025 2/2.14 |
| 2010/0198322 A1* | 8/2010 | Joseph ................... A61F 7/007 607/108 |
| 2011/0034887 A1* | 2/2011 | Forden ................. D06M 16/00 604/291 |
| 2015/0101788 A1 | 4/2015 | Smith et al. |
| 2015/0230527 A1* | 8/2015 | Branson ................ A41D 23/00 2/181 |
| 2017/0027053 A1* | 1/2017 | Moczygemba ......... F25B 21/02 |
| 2018/0147086 A1* | 5/2018 | Evans ...................... A61F 7/02 |

* cited by examiner

WEARABLE COOLING DEVICE

CROSS-REFERENCE TO RELATED APPLICATION

The present application claims priority benefit to a provisional patent application entitled "Wearable Cooling Device" which was filed on Jan. 29, 2018, and assigned Ser. No. 62/623,158. The entire content of the foregoing provisional patent application is incorporated herein by reference.

BACKGROUND

Wearable comfort, e.g., one's body temperature, is at the forefront of necessities and can be difficult to achieve in various environments, including indoor environments that share thermostats, e.g., office buildings or classrooms.

SUMMARY

The present disclosure relates to a wearable cooling device that is designed to rapidly restore and/or maintain a user's thermal comfort. The disclosed wearable cooling device is versatile and may be affixed to or in contact with (or close proximity to) a variety of locations on a user's body, e.g., wrist, neck and ankle, among others. For better results, the disclosed wearable cooling device is generally in direct contact with a user's skin; however, exemplary embodiments of the disclosed wearable cooling device are effective for use when not in direct contact with—but in proximity to—a user's skin.

In an exemplary embodiment, the wearable cooling device utilizes a forced air device, e.g., a fan, that blows air onto a wetted piece of media, e.g., fabric, which is in direct contact with a high thermally conductive element, e.g., copper or aluminum. The high thermally conductive element may be in contact with a user's skin or with a user's outer clothing. The wetted media is situated between the forced air device and the high thermally conductive element. When the forced air device is activated, the exhaust air passes onto and around the wetted media, which in turn cools the high thermally conductive element. As a result, the high thermally conductive element cools down the user.

Additional features, functions and advantages associated with the disclosed wearable cooling device will be apparent from the description which follows, particularly when read in conjunction with the appended figures.

BRIEF DESCRIPTION OF FIGURES

To assist those of ordinary skill in the art in making and using the disclosed wearable cooling device, reference is made to the appended figures, wherein.

DETAILED DESCRIPTION

Figure 1:
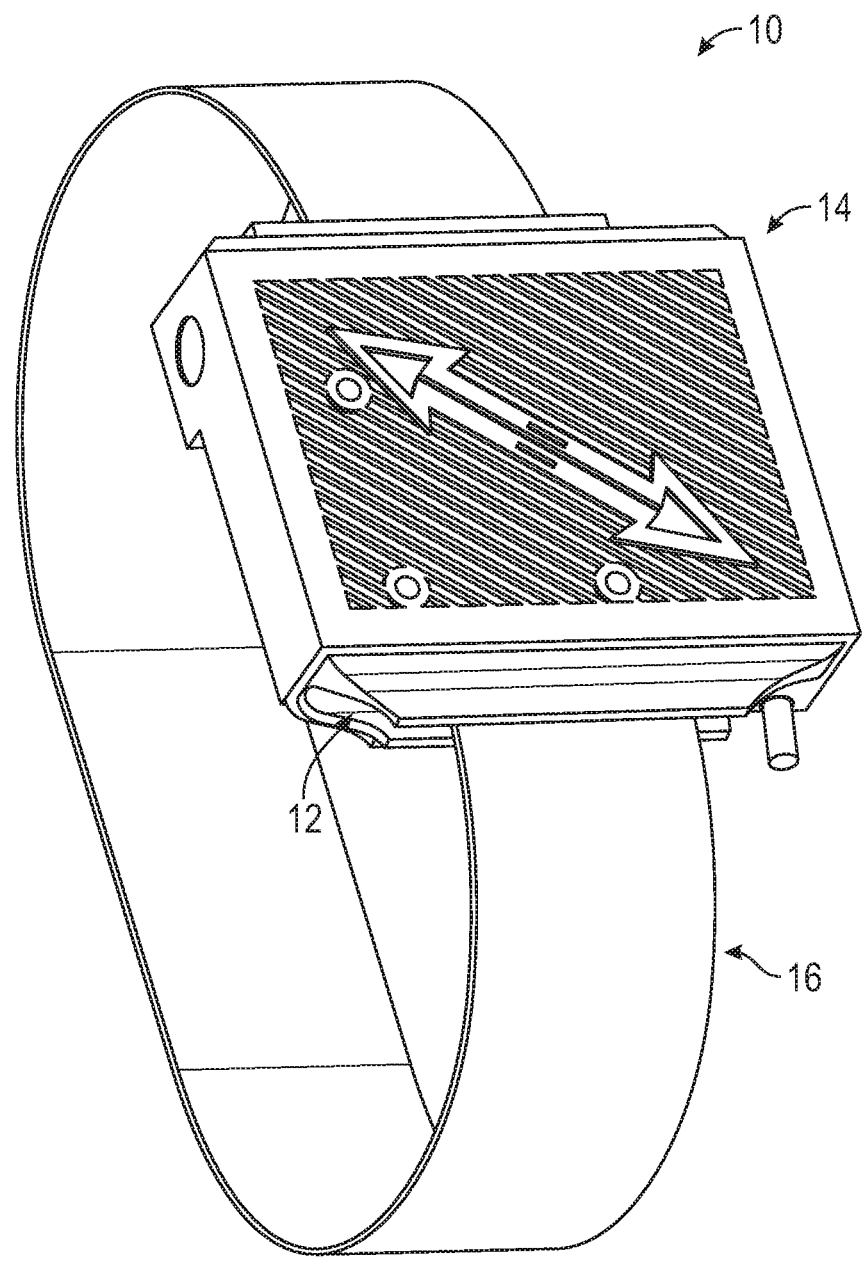
FIG. 1 is a photographic view of an exemplary wearable cooling device according to the present disclosure.

In an exemplary embodiment, a wearable cooling device according to the present disclosure includes a housing that encompasses at least one forced air device, e.g., a fan, and a wetted media, e.g., fabric, that is situated between the forced air device(s) and at least one high thermally conductive element. The wearable cooling device further generally includes a reservoir for holding a liquid that is wicked through the media. The reservoir is generally adapted to be refilled on an as-needed basis. In an exemplary embodiment, water is wicked through a fabric made from regenerated cellulose fiber, e.g., Rayon. However, additional liquid and media can be utilized, as will be apparent to persons skilled in the art.

As used herein, the term media refers to a material that may include at least one of the following structural forms: fabric, pad, woven, non-woven, solid, fibrous, perforated, permeable, impermeable, variable permeability, porous, non-porous, variable porosity, closed-cell foam, open-cell foam, layering, corrugate or flute, layers of corrugate or flute, cross-fluted structure (e.g., honeycomb), or a combination thereof. Such layers, corrugations, flutes, and cellular layers may be substantially parallel, perpendicular, or angled with reference to the direction of the forced air flow. However, additional media may be utilized without departing from the spirit/scope of this disclosure.

In an exemplary embodiment, the media may be absorbent and/or adsorbent. More particularly, the media may be an evaporative media that promotes evaporative cooling. The terms media and evaporative media may be used interchangeably without departing from the spirit/scope of this disclosure. The various structural forms, as mentioned above, may promote turbulent air flow in order to improve the liquid evaporation rate.

The media may be a combination of one or more synthetic and/or natural compositional components, such as in a homogenous or heterogeneous relationship, or a combination thereof. For example, the media may be fabricated from at least one of the following compositional components, including rayon, e.g., viscose, cotton, cellulose, sponge, pulp, fluff pulp, paper, polyethylene, polypropylene, polyethylene terephthalate, polyester, polyolefin, or a combination thereof. The above-mentioned components are merely examples to help persons skilled in the art design and fabricate the embodiments discussed in this disclosure; however, additional components may be used as will be apparent to persons skilled in the art. The media may further include, within and/or on one or more surfaces, a wetting aid, e.g., a surfactant, to reduce the surface tension of the media, thereby promoting additional wetting of the media.

Of note, the use of the term "liquid" also includes "evaporative liquid" and the terms may be used interchangeably without departing from the spirit/scope of the disclosure. The liquid may include water, alcohol, hygiene agents (as discussed below), or a combination thereof. A water blend may include a percentage of water that is greater than or less than the additional constituents. Specifically, water may constitute at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the liquid mass or liquid volume at room temperature, or decimal interval therein.

To reinforce the media when wet or dry, a media reinforcing material may be used to provide mechanical strength to the media. The media reinforcing material may be continuous or non-continuous through at least one portion of the media or may reinforce the entire media. For example, the media reinforcing material may include fibers, threads, strands, crystalline domains, scrims, netting, or a combination thereof. The composition of said media reinforcing material may include synthetic or natural material components, including rayon, e.g., viscose, cotton, cellulose, sponge, pulp, fluff pulp, paper, polyethylene, polypropylene, polyethylene terephthalate, polyester, polyolefin, fiberglass, metal (e.g., aluminum, copper, steel), glass, or a combination thereof. The above-mentioned media reinforcing materials are merely examples to help persons skilled in the art design and fabricate the embodiments discussed in this disclosure; however, additional media reinforcing materials may be used as will be apparent to persons skilled in the art. The media reinforcing material may further retain and/or transport liquid(s), including evaporative liquid(s), however, retention and/or transportation of liquid(s) is not required.

In another exemplary embodiment, the media may include, e.g., treated with, one or more hygiene maintenance agents. The term hygiene maintenance agents, as used herein, refers to a material or chemical that deters and/or eliminates the formation of unwanted/unhealthy biological organisms. The material or chemical may be included in, on the surface of, or in close proximity to the media and/or the liquid. For example, the hygiene maintenance agent may include bactericides, anti-microbial agents, germicides, herbicides, antibiotics, antivirals, biocides, fungicides, antifungals, algicides, anti-fouling agents, insecticides, pesticides, antiparasites, disinfectants, vinegar, or a combination thereof. The above-mentioned hygiene maintenance agents are merely examples to help persons skilled in the art design and fabricate the embodiments discussed in this disclosure; however, additional hygiene maintenance agents may be used as will be apparent to persons skilled in the art.

In an exemplary embodiment, the amount of the hygiene maintenance agent within the media and/or within the liquid will evaporate and/or be consumed at a rate similar to the liquid. More preferably, the hygiene maintenance agent will be consumed and/or evaporated at a rate less than the liquid; without substantially affecting the hygienic performance characteristics of the hygiene maintenance agent. If incorporated within the liquid, the hygiene maintenance agent may be combined at a ratio of 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 100:1, 99:1, 98:1, 97:1, 96:1, 95:1, 94:1, 93:1, 92:1, 91:1, 90:1, 89:1, 88:1, 87:1, 86:1, 85:1, 84:1, 83:1, 82:1, 81:1, 80:1, 79:1, 78:1, 77:1, 76:1, 75:1, 74:1, 73:1, 72:1, 71:1, 70:1, 69:1, 68:1, 67:1, 66:1, 65:1, 64:1, 63:1, 62:1, 61:1, 60:1, 59:1, 58:1, 57:1, 56:1, 55:1, 54:1, 53:1, 52:1, 51:1, 50:1, 49:1, 48:1, 47:1, 46:1, 45:1, 44:1, 43:1, 42:1, 41:1, 40:1, 39:1, 38:1, 37:1, 36:1, 35:1, 34:1, 33:1, 32:1, 31:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or a decimal interval therein.

Furthermore, as used herein, the term "high thermally conductive element" refers to an element, e.g., material, that rapidly transfers heat sufficient to enhance the ability of the media to evaporate the liquid. The high thermally conductive element may include aluminum, beryllium, bismuth, bronze, chromium, copper, gallium, iron, lead, magnesium, manganese, silicon, titanium, vanadium, zinc, zirconium, or a combination thereof. In exemplary embodiments, the high thermally conductive element is fabricated from aluminum and copper alloys. The above-mentioned materials are merely examples to help persons skilled in the art design and fabricate the embodiments discussed in this disclosure; however, additional materials may be used as will be apparent to persons skilled in the art. The high thermally conductive element may be in the form of a solid, band, ribbon, weave, braid, strand, or a combination thereof. Of note, the terms "high thermally conductive element," "conductive element," and any other variation are used interchangeably without departing from the spirit/scope of the disclosure. In an exemplary embodiment, the high thermally conductive element has a thermal conductivity of at least 50 watts/meter-Kelvin, at a temperature between 273 Kelvin ("K") to 300 K and at atmospheric pressure. More preferably, the thermal conductivity is 50 watts/meter-K to 425 watts/meter-Kelvin. Additionally, the high thermally conductive element may be non-metallic and may include carbon nanotube and graphene structures.

The disclosed wearable cooling device is versatile and may be affixed to or in contact with (or close proximity to) a variety of locations on a user's body, e.g., wrist, neck, ankle, among others. The disclosed wearable cooling device may be attached with respect to a user's body in various ways, e.g., by one or more straps, clips, belts, lanyards and/or similar attachment means as will be apparent to persons skilled in the art.

Of note, the use of the term "body" does not necessarily only include a user's skin, but can also include a user's clothing or other outer garments. The preferred location on a user's body should be close to or in contact with a portion of the circulatory system, e.g., arteries or veins, specifically because the human (and other mammals') body is more sensitive in those locations and will experience thermal comfort quicker. However, the present disclosure is not limited by or to such preferred positioning of the disclosed device.

Figure 2:
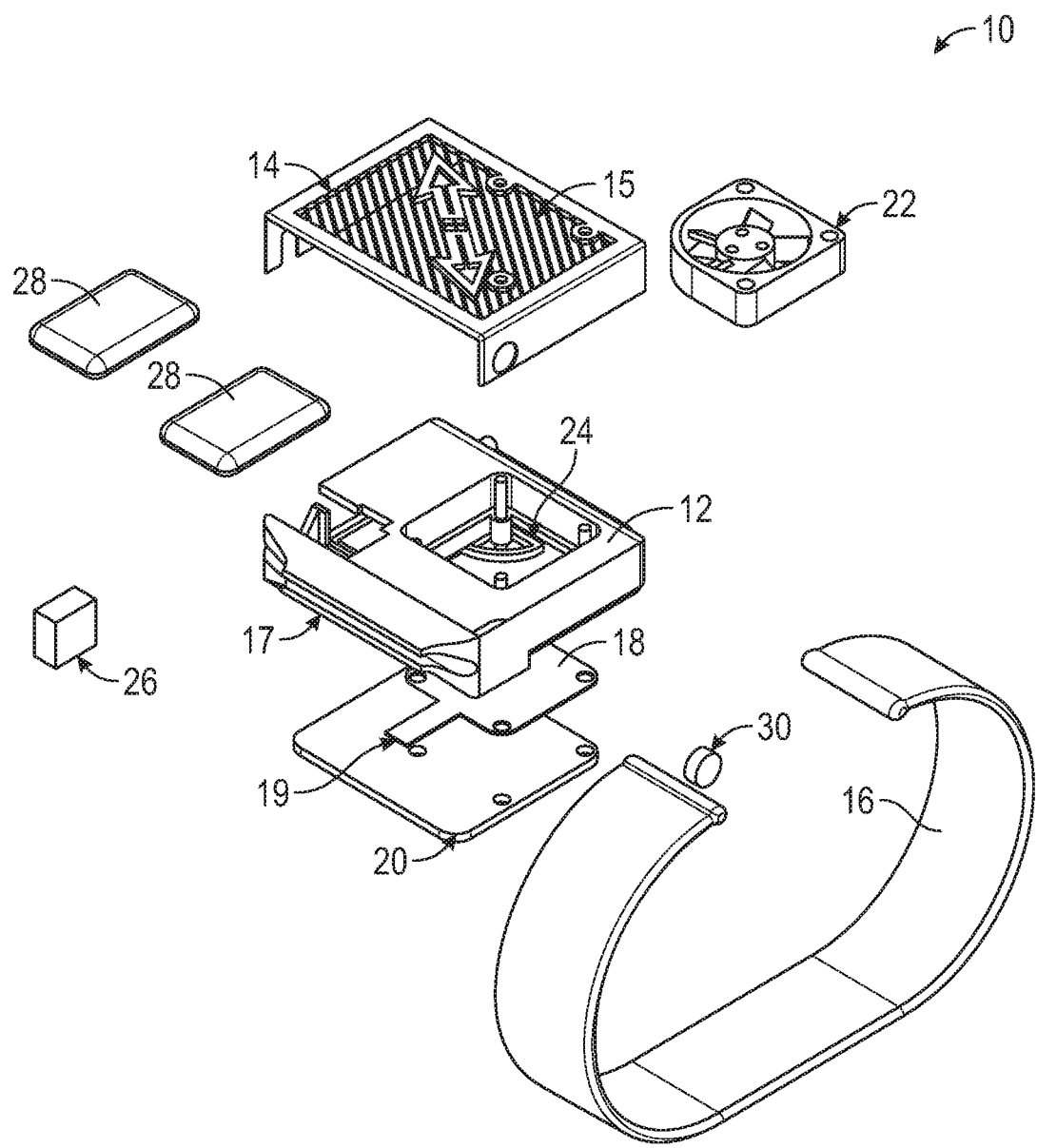
FIG. 2 is a schematic drawing of an exemplary wearable cooling device according to the present disclosure.
Figure 3:
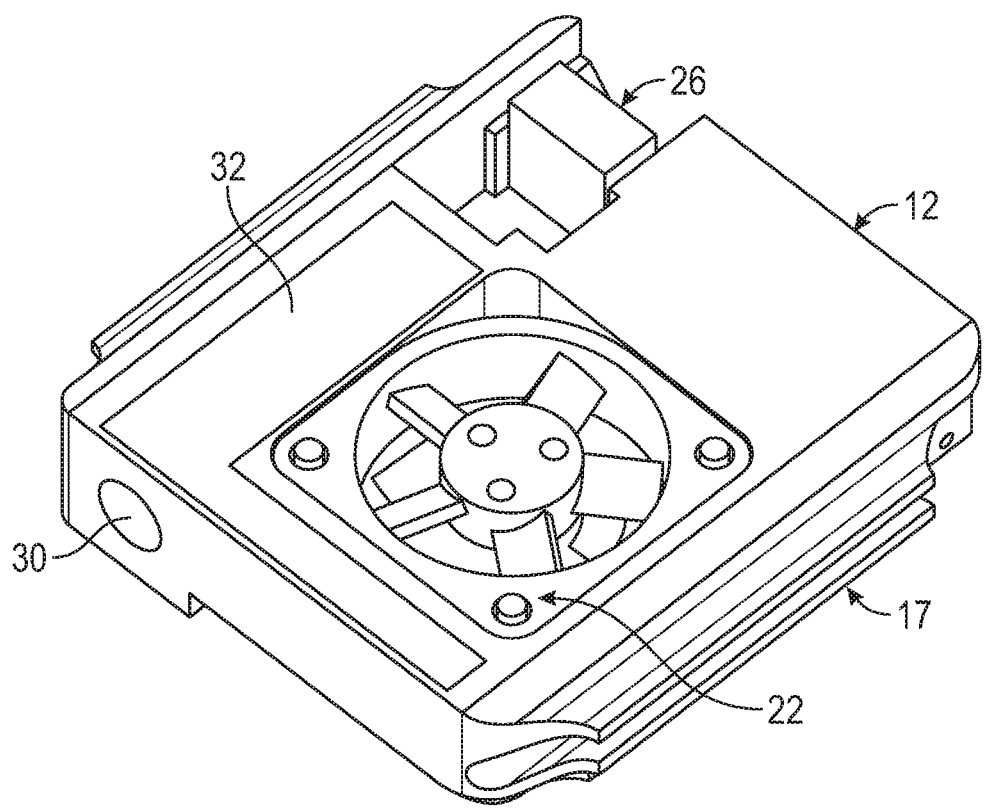
FIG. 3 is a cross-sectional schematic drawing of an exemplary housing of a wearable cooling device according to the present disclosure.

With reference to FIGS. 1-3, an exemplary embodiment of the disclosed wearable cooling device 10 is schematically depicted. In the exemplary embodiment, the wearable cooling device 10 is intended to be worn on the inside portion of a user's wrist. Strap 16 connects to two opposing edges of housing 12 and forms a loop, adjustable in diameter, so as to fit any wrist size. Strap 16 resembles a watch strap and can be a single loop expandable strap, e.g., a flexible material, or two separate straps that connect together around any size wrist; e.g., with a clasp or a hook and loop attachment mechanism. In one embodiment, each end of strap 16 slides into a complementary slot 17, e.g., a radiused slot, that is located on two opposing edges of housing 12. Complementary slot 17 promotes changeability of various strap 16 designs.

Cover 14 is provided for detachable attachment to housing 12 so as to encase certain internal components of device 10. In the exemplary embodiment depicted in FIGS. 1-3, cover 14 features several slats 15 that enable the forced air device (not pictured) to pull fresh air from outside housing 12 to force through at least a portion of wearable cooling device 10. In the exemplary embodiment, slats 15 are angularly oriented relative to the sides of cover 14. However, alternative venting features may be incorporated into cover 14 to permit forced air flow therethrough, as will be readily apparent to persons skilled in the art.

FIG. 2 schematically depicts exemplary wearable cooling device 10 in an exploded view. In an exemplary embodiment, media 18 is situated between housing 12 and high thermally conductive element 20, e.g., copper. In an exemplary embodiment, a media regenerated from purified cellulose, e.g., dissolving wood pulp, may be used. Rayon, e.g., Lyocell, is a high absorbent media that further provides for an even liquid distribution throughout the media and features strong mechanical properties when wet. However, additional and/or alternative media or materials may be utilized, as discussed above, and as will be apparent to persons skilled in the art. Of note, a material with strong mechanical properties refers to a material that maintains and/or improves its mechanical properties, e.g., structural and visual integrity, prior to, during, and/or after operation(s). Specifically, media 18 is in contact with a liquid release outlet (not pictured) of a reservoir (not pictured) located within housing 12. A liquid, e.g., water, is then transported from the reservoir and through the liquid release outlet into contact with media 18. Such transportation may be accomplished through wicking, including capillary action and/or surface tension transport, among others.

In the exemplary embodiment, media 18 is substantially square in geometry, but features tab portion 19 that captures the liquid from the liquid release outlet (not pictured) and evenly distributes the liquid through at least a portion of media 18. A sealed connection between tab portion 19 and the liquid release outlet ensures effective transfer of liquid from the reservoir (not pictured) to media 18. In an exemplary embodiment, the reservoir is lined with media 18 to promote liquid transportation in any orientation. The flow of the liquid is controlled by the inherent properties of media 18. Specifically, since media 18 promotes wicking of the liquid, media 18 thus extracts the liquid from the reservoir to prevent drying out.

Forced air device 22, e.g., a fan, is positioned within cavity 24 formed or defined in housing 12. Cavity 24 features a mounting interface to capture forced air device 22 and a semi-exposed base that facilitates airflow pass-through. In an exemplary embodiment, forced air device 22 blows air through the semi-exposed base onto the wetted media 18, which in turn cools down media 18 through liquid evaporation and associated heat release through such phase change operation. Since high thermally conductive element 20 is in contact with the cooled down media 18, high thermally conductive element 20 subsequently cools down as a result of its thermal conductive properties. More particularly, in connection with the liquid vaporization, heat is transferred from thermally conductive element 20, thereby causing thermally conductive element 20 to cool down. The user generally does not feel any wetness on his/her skin, but merely feels the coolness of high thermally conductive element 20.

To ensure the inlet to forced air device 22 has proper air flow, cover 14 includes slats 15 or other airflow opening(s) that partially expose forced air device 22 to ambient air. Furthermore, excess exhaust air from forced air device 22 that does not contact media 18 and/or high thermally conductive element 20 can provide additional cooling to a user. Forced air device 22 may be adjustably controlled by a potentiometer 26 that is mounted within housing 12. Additional control features may be incorporated, as will be apparent to persons skilled in the art.

To power forced air device 22, at least one battery 28 is electrically generally connected to the components. Additional batteries 28, as pictured, may be incorporated based on electrical requirements. Battery 28 may be rechargeable or disposable. Furthermore, for those users that are close to an external power source, e.g., computer or wall plug, wearable cooling device 10 may be charged and/or powered by plugging the device in.

In an exemplary embodiment, wearable cooling device 10 features feedback capabilities. A temperature sensing device (not pictured) may be affixed to high thermally conductive element 20 to measure the user's skin temperature. When wearable cooling device 10 is not active, but is in direct contact with the user's skin (or in close proximity thereto), the temperature of high thermally conductive element 20 would reflect the user's skin temperature. Wearable cooling device 10 may further include a controller (not pictured) to receive the user's skin temperature measurement, compare that measurement with predetermined individualized temperature thresholds, and respond accordingly. For instance, if the user's skin temperature is above the user's predetermined temperature threshold, a signal may be sent to the controller to activate forced air device 22 to cool down the user and/or to change the operating speed of forced air device 22. Similarly, the signal can cause a modification to the airflow passage(s), e.g., by partially opening or closing the passage(s) to permit greater or lesser airflow therethrough.

In another exemplary embodiment of the present disclosure, an additional sensor may be attached to cover 14 to measure the ambient temperature of a room. In doing so, the wearable cooling device 10 would resemble a thermostat, predicting, based on the ambient temperature of the room and the user's skin temperature, when forced air device 22 should activate and for what duration. Furthermore, in another embodiment, wearable cooling device 10 may include a heating element (not pictured) that would heat a portion of the device and transfer that heat through high thermally conductive element 20 to the user. The heating element (not pictured) may be incorporated within wearable cooling device 10 to heat the liquid prior to contacting media 18. The heating element (not pictured) may also be attached to media 18 to heat media 18 after it has been exposed to the liquid.

FIG. 3 depicts a cross-section of an assembled housing 12 according to the present disclosure. As was previously discussed, forced air device 22 interfaces with the dimensionally similar cavity of housing 12. Substantially surrounding forced air device 22 is reservoir 32. The volume of liquid within reservoir 32 depends on the size of wearable cooling device 10. For example, wearable cooling device 10 to be worn on a user's wrist may have 5 milliliters ("mL") of liquid. The reservoir volume, however, regardless of wearing location, may be 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, 30 mL, or a greater volume that exceeds 30 mL, and any interval in between. Furthermore, incorporated into a side wall of housing 12, that abuts reservoir 32, is a reservoir plug 30 that provides access to reservoir 32, e.g., filling or emptying the reservoir.

Although the present disclosure has been described with reference to exemplary implementations, the present disclosure is not limited by or to such exemplary implementations. Rather, various modifications, refinements and/or alternative implementations may be adopted without departing from the spirit or scope of the present disclosure.

The invention claimed is:

1. A wearable device, comprising:
    a housing defining a reservoir for receipt of a liquid;
    a forced air device positioned within the housing;
    a thermally conductive element mounted with respect to the housing and positioned for thermal interface with the skin of a user, the thermally conductive element having a thermal conductivity of 50-425 watts/meter-Kelvin, at a temperature between 273° K and 300° K, which enables heat transfer away from the skin of the user for the user to feel a coolness from contact with the thermally conductive element;
a wetted media positioned within the housing, the wetted media (i) in fluid communication with liquid received by the reservoir, and (ii) in direct contact with the thermally conductive element for direct thermal communication with the thermally conductive element; and
means for detachably securing the housing relative to a user;
wherein the thermal conductivity of the thermally conductive element enables the thermally conductive element to cool down based on heat transfer to the wetted media, and
wherein operation of the forced air device effects evaporative cooling through liquid evaporation from the wetted media and, based on direct thermal communication between the wetted media and the thermally conductive element, effects cooling of the thermally conductive element positioned for thermal interface with the skin of the user.

2. The wearable device according to claim 1, wherein the forced air device is a fan.

3. The wearable device according to claim 1, wherein the thermally conductive element is fabricated in whole or in part from the group consisting of aluminum, beryllium, bismuth, bronze, chromium, copper, gallium, iron, lead, magnesium, manganese, silicon, titanium, vanadium, zinc, zirconium, carbon nanotube, graphene, and any combination thereof.

4. The wearable device according to claim 1, wherein the wetted media is fabricated in whole or in part from the group consisting of fabric, pad, woven, non-woven, solid, fibrous, perforated, permeable, impermeable, variable permeability, porous, non-porous, variable porosity, closed-cell foam, open-cell foam, layering, corrugate or flute, layers of corrugate or flute, cross-fluted structure, and any combination thereof.

5. The wearable device according to claim 1, wherein the wetted media is highly absorbent and equally distributive.

6. The wearable device according to claim 1, wherein the wetted media is fabricated in whole or in part from the group consisting of rayon, viscose, cotton, cellulose, sponge, pulp, fluff pulp, paper, polyethylene, polypropylene, polyethylene terephthalate, polyester, polyolefin, and any combination thereof.

7. A wearable device according to claim 1, wherein the reservoir is configured and dimensioned to receive 5 milliliters of liquid.

8. The wearable device according to claim 1, wherein the means for detachably securing the housing to a user is selected from the group consisting of a strap and a clip.

9. The wearable device according to claim 1, wherein the device contains a temperature sensor.

10. The wearable device according to claim 1, wherein the device further includes a heating device.

11. The wearable device according to claim 1, further comprising a control system for (i) measuring at least one of a temperature of the user's skin and an ambient temperature, and (ii) controlling operation of the forced air device in response to the measured temperature.

12. The wearable device according to claim 1, wherein the liquid is comprised in whole or in part from the group consisting of water, alcohol, hygiene agents, and any combination thereof.

13. The wearable device according to claim 1, further comprising a media reinforcing material for providing mechanical strength to the wetted media.

14. The wearable device according to claim 13, wherein the media reinforcing material is fabricated in whole or in part from the group consisting of fibers, threads, strands, crystalline domains, scrims, netting, and any combination thereof.

15. The wearable device according to claim 13, wherein the media reinforcing material is fabricated in whole or in part from the group consisting of rayon, viscose, cotton, cellulose, sponge, pulp, fluff pulp, paper, polyethylene, polypropylene, polyethylene terephthalate, polyester, polyolefin, fiberglass, metal, aluminum, copper, steel, glass, and any combination thereof.

16. The wearable device according to claim 1, further comprising a hygiene maintenance agent for deterring and/or eliminating the formation of unwanted/unhealthy biological organisms.

17. The wearable device according to claim 16, wherein the hygiene maintenance agent is formulated in whole or in part from the group consisting of bactericides, anti-microbial agents, germicides, herbicides, antibiotics, antivirals, biocides, fungicides, antifungals, algicides, anti-fouling agents, insecticides, pesticides, antiparasites, disinfectants, vinegar, and any combination thereof.

18. The wearable device according to claim 1, further comprising at least one battery positioned within the housing in physical proximity to and in electrical communication with the forced air device.

19. A method for adjusting skin temperature conditions, the method comprising:
detachably securing a wearable device in contact or in close proximity to the skin of a user, the wearable device including (i) a housing defining a reservoir containing a liquid, (ii) a forced air device positioned within the housing, (iii) a thermally conductive element mounted with respect to the housing and positioned for thermal interface with the skin of a user, the thermally conductive element having a thermal conductivity of 50-425 watts/meter-Kelvin, at a temperature between 273° K and 300° K, and (iv) a wetted media positioned within the housing, the wetted media in fluid communication with liquid received by the reservoir, and in direct contact with the thermally conductive element for direct thermal communication with the thermally conductive element;
activating the forced air device of the wearable device to adjust the user's skin conditions, wherein the wearable device adjusts the user's skin conditions based on forced air passage over the wetted media that is in fluid contact with the liquid, and effectuating a cooling effect based on direct heat transfer from the thermally conductive element to the wetted media and vaporization of the liquid from the wetted media to effect evaporative cooling;
wherein the thermal conductivity of the thermally conductive element enables the thermal conductive element to cool down based on heat transfer to the wetted media.

20. The method according to claim 19, wherein the forced air device is a fan.

21. The method according to claim 19, wherein the wearable device includes a temperature sensor that is positioned so as to measure at least one of (i) a temperature of the user's skin, or (ii) ambient conditions, and further comprising adjusting operation of the forced air device in response to the measured temperature.

22. The method according to claim 19, wherein the wearable device further comprises at least one battery positioned within the housing in physical proximity to and in electrical communication with the forced air device.

* * * * *